United States Patent [19]

Buxbaum

[11] 4,341,693

[45] Jul. 27, 1982

[54] OLIGOMERIC EPOXIDE RESINS AND THEIR USE AS FLAMEPROOFING AGENTS

[75] Inventor: Lothar Buxbaum, Villach, Austria

[73] Assignee: Ciba-Geigy Corporation, Ardsley, N.Y.

[21] Appl. No.: 273,799

[22] Filed: Jun. 15, 1981

[30] Foreign Application Priority Data

Jun. 26, 1980 [CH] Switzerland ............... 4914/80

[51] Int. Cl.³ ................... C08G 59/26; C08G 5/34
[52] U.S. Cl. ................... 524/93; 106/15.05; 252/609; 525/107; 528/87; 528/96; 528/117; 528/363; 528/367; 548/305
[58] Field of Search ............... 260/18 EP, 45.8 AH, 260/45.8 NH; 528/87, 96, 117, 363, 367; 106/15.05; 525/107; 252/609; 548/305

[56] References Cited

U.S. PATENT DOCUMENTS

| | | |
|---|---|---|
| 2,602,075 | 7/1952 | Carpenter et al. . |
| 3,306,872 | 2/1967 | Maycock et al. . |
| 3,495,255 | 2/1970 | George ............... 528/117 |
| 3,843,674 | 10/1974 | Porret . |
| 3,939,125 | 2/1976 | Porret ............... 528/367 |
| 3,943,109 | 3/1976 | Porret . |
| 3,954,790 | 5/1976 | Habermeier . |
| 4,315,849 | 2/1982 | Buxbaum et al. . |

OTHER PUBLICATIONS

Lemper et al., "Linear Aromatic Polyesters", Chemical Abstracts 85, 124630e (1976).
CA, 95, 26060f (1981).

*Primary Examiner*—Earl A. Nielsen
*Attorney, Agent, or Firm*—Luther A. R. Hall

[57] ABSTRACT

Oligomeric, essentially linear epoxide resins with chlorine-containing and/or bromine-containing benzimidazolone radicals in the oligomer chain are particularly suitable as flameproofing agents for thermosetting and thermoplastic polymers.

10 Claims, No Drawings

OLIGOMERIC EPOXIDE RESINS AND THEIR USE AS FLAMEPROOFING AGENTS

The present invention relates to halogen-containing, essentially linear, oligomeric epoxide resins which contain halogenated benzimidazolone groups, and their use as flameproofing agents in polymers.

Many halogen-containing organic compounds, which are used either by themselves or, usually, together with synergistic agents, such as N compounds, P compounds or antimony compounds, have already been proposed as flameproofing agents for polymers. The known halogen-containing compounds cannot always fulfil the requirements placed on them in respect of extraction and migration properties, heat stability, the absence of an effect on the substrate properties and the effect of corrosion of metals with which the substrate provided with a flamerepellent finish comes into contact.

The object of the present invention is to provide flameproofing agents which fulfil these requirements.

The present invention relates to halogen-containing, essentially linear, oligomeric epoxide resins of the formula I

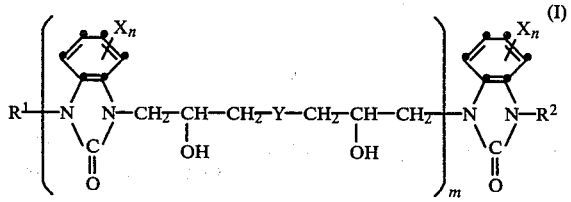

in which n is the number 2, 3 or 4, m has a numerical value from 1 to 30, X is chlorine or bromine, Y is the divalent radical of a H-acid compound from the group comprising diols, dihydric phenols, bisphenols, dicarboxylic acids and cyclic ureides and $R^1$ and $R^2$ are H atoms,

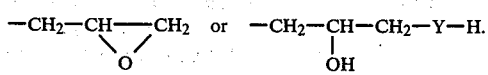

Preferably, in formula I, n is 3 and, in particular, 4 and m has a numerical value from 1 to 20, in particular from 1 to 10. X is preferably bromine.

Y in formula I can be the divalent radical of a diol having, preferably, 2-12 C atoms. It can be a linear or branched alkylenediol which is interrupted by N-heterocyclic groups, cycloalkylene groups or O atoms, or a cycloaliphatic diol. Examples are ethylene glycol, 1,2- or 1,3-propanediol, 1,2-, 1,3- or 1,4-butanediol, 1,5-pentanediol, hexanediol, decanediol, dodecanediol, diethylene glycol, triethylene glycol, dipropylene glycol, 1,4-dihydroxymethylcyclohexane, 1,4-dihydroxycyclohexane, N,N'-bis-(β-hydroxyethyl)-5,5-dimethylhydantoin and N,N'-bis-(β-hydroxyethyl)-tetrachloro- or -tetrabromobenzimidazolone.

A divalent radical Y of a dicarboxylic acid can be derived from an aliphatic, cycloaliphatic or aromatic dicarboxylic acid, preferably having 2 to 20 and in particular 4 to 16 C atoms. Examples are: oxalic acid, malonic acid, ethylmalonic acid, dodecylmalonic acid, succinic acid, decylsuccinic acid, glutaric acid, adipic acid, trimethyladipic acid, pimelic acid, suberic acid, azelaic acid, sebacic acid, octadecanedicarboxylic acid, dimer acids (dimerisation products of olefinically unsaturated $C_{10}$–$C_{20}$-fatty acids), cyclohexane-1,4-dicarboxylic acid, phthalic acid, isophthalic acid, terephthalic acid, 4,4'-diphenyldicarboxylic acid and 4,4'-carboxydiphenyl ether.

A radical Y of a dihydric phenol can be derived from unsubstituted or $C_1$–$C_4$-alkyl-substituted hydroquinone, pyrocatechol or resorcinol.

A divalent radical Y of a bisphenol preferably has the formula II

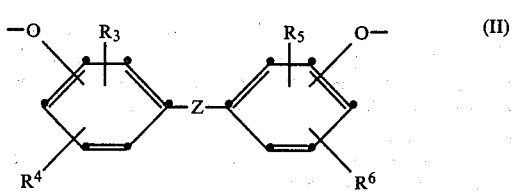

in which $R^3$, $R^4$, $R^5$ and $R^6$ independently of one another are a hydrogen atom, alkyl having 1–4 C atoms or a chlorine or bromine atom and Z is a direct bond, O, S, SO, $SO_2$, $CO_2$, alkylene having 1 to 8 C atoms, alkylidene having 2–8 C atoms or cycloalkylidene having 5 or 6 ring C atoms.

The substituents $R^3$, $R^4$, $R^5$ and $R^6$ are preferably bonded in the ortho-position relative to the oxygen atom, and the oxygen atom is preferably in the meta-position or, particularly preferably, in the para-position relative to the group Z. An alkylene group Z preferably has 1 to 4 C atoms, and an alkylidene group Z preferably has 2 to 6 C atoms. Examples of alkylene are methylene, ethylene, 1,2- or 1,3-propylene, butylene and hexylene. Examples of alkylidene and cycloalkylidene are ethylidene, 2-chloro-1,1-ethylidene, 2,2-dichloro-1,1-ethylidene, 2,2,2-tri-chloro-1,1-ethylidene, 1,1- or 2,2-propylidene, 1,1- or 2,2-butylidene, pentylidene, hexylidene, octylidene, cyclopentylidene and cyclohexylidene.

Examples of bisphenols are 4,4'-dihydroxydiphenyl, bis-(p-hydroxyphenyl)-methane, 1,1-bis-(p-hydroxyphenyl)-cyclohexane, 2,2-bis-(p-hydroxyphenyl)-propane, 2,2-bis-(4-hydroxy-3,5-dibromophenyl)-propane and 4,4'-dihydroxydiphenyl ether. Further examples are listed in German Offenlegungsschrift No. 2,601,960.

A divalent radical Y of a cyclic ureide preferably has one of the formulae III to VII

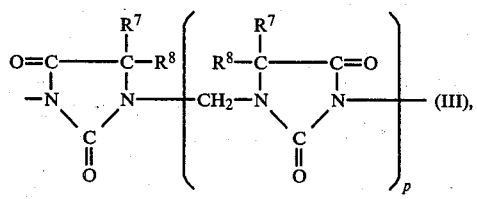

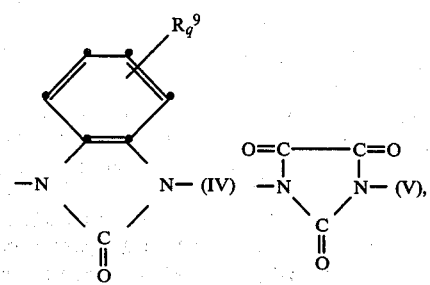

-continued

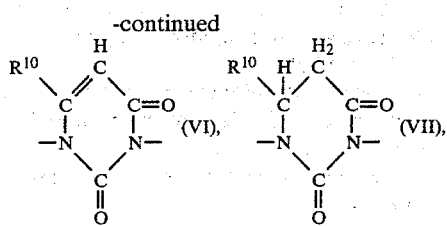

in which p is 0 or 1, q is 0 or an integer from 1 to 4, $R^7$ and $R^8$ are hydrogen atoms, phenyl or $C_1$–$C_{12}$-alkyl or $R^7$ and $R^8$ together are tetra- or penta-methylene, $R^9$ is methyl, chlorine or bromine and $R^{10}$ is a hydrogen atom or $C_1$–$C_4$-alkyl.

$R^7$ and $R^8$ in formula III are preferably hydrogen atoms, phenyl or $C_1$–$C_4$-alkyl, such as methyl, ethyl, n-propyl, i-propyl, n-butyl, i-butyl or t-butyl. In formula IV, q is preferably 3, and particularly preferably 4, and $R^9$ is preferably chlorine, and particularly preferably bromine. Examples of $R^{10}$ are butyl, n-propyl, ethyl and methyl. $R^{10}$ is preferably a hydrogen atom or methyl.

Epoxide resins of the formula I in which n is 4, m has a numerical value from 1 to 10, X is bromine and Y is a radical of the formula IV, in which $R^9$ is chlorine or, in particular, bromine and q is the number 3 or, in particular, 4, have proved particularly valuable.

The epoxide resins according to the invention are prepared by known processes of the state of the art in the industrial equipment customary for these processes.

In one embodiment, a chlorinated or brominated N,N'-diglycidylbenzimidazolone of the formula

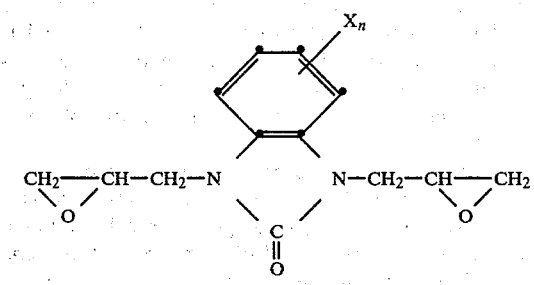

can be reacted with a bifunctional H-acid compound H-Y-H, in which X, n and y are as defined above.

This reaction, which is described as an advancement process in U.S. Pat. No. 3,306,872, can be carried out in the absence or presence of a preferably polar aprotic solvent, such as an ether (tetrahydrofuran, dioxane or dibutyl ethers), sulfone (dimethylsulfoxide), ketone or carboxylic acid amide (dimethylformamide). The molar ratio of diglycidyl compound to H-acid compound can be 2:1 to 1:2, preferably 1.5:1 to 1:1.5. This reaction temperature is from 100° to 250° C. and the reaction time can be up to 5 hours or more, depending on the desired degree of oligomerisation, which can be determined via the viscosity of the reaction product.

The reaction can be accelerated with catalysts. Such curing accelerators are generally used in amounts of 0.1 to 5, preferably 0.1 to 2, % by weight, based on the reactants. Those compounds which are capable of accelerating the curing reaction are suitable. Examples are:

Imidazole and its homologues as well as salts thereof with polycarboxylic acids or their anhydrides, such as imidazole, 1-methylimidazole, 2-ethylimidazole, 2-methyl-4-ethylimidazole, 2-phenylimidazole and benzo- triazole, organic phosphorus compounds, $BF_3$ or $BCl_3$ complexes, organic phosphonium borates, alkylammonium halides (for example the chlorides and bromides), such as tetramethylammonium chloride, and ureas and derivatives, such as N-p-chlorophenyl-N,N'-dimethylurea. The imidazoles are preferred.

In a further embodiment for the preparation of the oligomers according to the invention, it is also possible to react the bis-glycidyl derivatives of the H-acid compounds having the formula

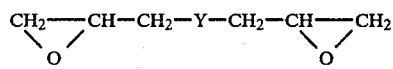

with chlorinated or brominated benzimidazoles of the formula

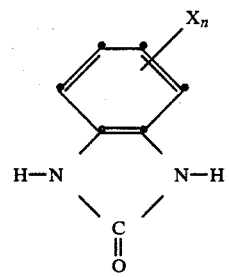

under similar reaction conditions. This reaction is also an advancement process, as described in U.S. Pat. No. 3,306,872.

In another embodiment for the preparation of the oligomers according to the invention, it is also possible for a chlorinated or brominated benzimidazolone and a H-acid compound to be reacted directly with epichlorohydrin (Taffy process, compare U.S. Pat. No. 2,602,075).

The partially chlorinated benzimidazolone-bis-glycides used as starting materials are known from German Offenlegungsschrift No. 2,300,010. The partially brominated and the completely chlorinated or brominated benzimidazolone-bis-glycides are new and are prepared by analogous processes.

The epoxide resins according to the invention are essentially linear oligomers. Crosslinking reactions via the secondary OH group formed in the addition reaction are observed only to a very slight degree. The oligomers have a liquid to viscous or resinous consistency, and can have a relative viscosity of up to 1.3. The high-melting compounds also have an excellent stability to heat.

The epoxide resins according to the invention are outstandingly suitable as flameproofing agents for plastics, since little corrosive vapour is evolved when they are warmed and they therefore cause less damage to metals with which they are in contact. Their high resistance to migration is also a considerable advantage. It should also be emphasised that, as a result of being sparingly soluble, the compounds are stable to extraction.

The present invention furthermore relates to a composition of a plastic, which contains a thermosetting resin or a thermoplastic and an effective amount of an epoxide resin of the formula I, as a flameproofing agent.

Amounts of 0.1 to 30% by weight, preferably 1 to 15% by weight, based on the plastic, are generally incorporated into the plastic. The flameproofing agent can be used by itself or, preferably, together with about 0.1 to 20% by weight, in particular 1 to 15% by weight, based on the plastic, of a compound of an element of main group V of the periodic system, which has a synergistic action. In addition to nitrogen compounds or phosphorus compounds, antimony compounds, for example antimony trioxide, are particularly suitable.

Plastics are either thermosetting resins or thermoplastics. Thermoplastics are preferred.

Examples are:
1. Polymers which are derived from mono- or di-unsaturated hydrocarbons, such as polyolefins, for example polyethylene, which can be non-crosslinked or crosslinked, polypropylene, polyisobutylene, polymethylbut-1-ene, polymethylpent-1-ene, polybut-1-ene, polyisoprene, polybutadiene, polystyrene and polyisobutylene, copolymers of the monomers on which the homopolymers mentioned are based, such as ethylene/propylene copolymers, propylene/but-1-ene copolymers and propylene/isobutylene copolymers, and terpolymers of ethylene, propylene and a diene, for example hexadiene, dicyclopentadiene or ethylidene-norbornene, and mixtures of the above-mentioned homopolymers, for example mixtures of polypropylene and polyethylene, polypropylene and polybut-1-ene, and polypropylene and polyisobutylene.
2. Halogen-containing vinyl polymers, such as polyvinyl chloride, polyvinylidene chloride and polyvinyl fluoride, as well as polychloroprene and chlorinated rubbers.
3. Polymers which are derived from $\alpha,\beta$-unsaturated acids and derivatives thereof, such as polyacrylates and polymethacrylates, polyacrylamides and polyacrylonitrile, as well as copolymers thereof with other vinyl compounds, such as acrylonitrile/butadiene/styrene copolymers, acrylonitrile/styrene copolymers and acrylonitrile/styrene/acrylate copolymers.
4. Polymers which are derived from unsaturated alcohols and amines or their acyl derivatives or acetals, such as polyvinyl alcohol, polyvinyl acetate, stearate, benzoate or maleate, polyvinyl butyral, polyallyl phthalate and polyallylmelamine, and copolymers thereof with other vinyl compounds, such as ethylene/vinyl acetate copolymers.
5. Homopolymers and copolymers which are derived from epoxides, such as polyethylene oxide, or the polymers which are derived from polyglycidyl compounds.
6. Polyacetals, such as polyoxymethylene and polyoxyethylene, as well as those polyoxymethylenes which contain ethylene oxide as a comonomer.
7. Polyphenylene oxides.
8. Polyurethanes and polyureas.
9. Polycarbonates.
10. Polysulfones.
11. Polyamides and copolyamides which are derived from diamines and dicarboxylic acids and/or from aminocarboxylic acids or the corresponding lactams, such as polyamide 6, polyamide 6/6, polyamide 6/10, polyamide 11 or polyamide 12; this is a preferred group of plastics.
12. Crosslinked polymers which are derived from aldehydes on the one hand and phenols, ureas or melamines on the other hand, such as phenol/formaldehyde resins, urea/formaldehyde resins and melamine/formaldehyde resins.
13. Alkyd resins, such as glycerol/phthalic acid resins, and mixtures thereof with melamine/formaldehyde resins.
14. Unsaturated polyester resins which are derived from copolyesters of saturated and unsaturated dicarboxylic acids and polyhydric alcohols, as well as vinyl compounds as crosslinking agents.
15. Natural polymers, such as cellulose and rubber, and polymer-homologous chemically modified derivatives thereof, such as cellulose acetates, propionates and butyrates, and the cellulose ethers, such as methylcellulose.
16. Thermoplastic polyesters based on aliphatic, cycloaliphatic and/or aromatic dicarboxylic acids and aliphatic, cycloaliphatic and/or aromatic diols.

Polyesters which contain at least 25 mol %, preferably 40 mol %, of terephthalic acid radicals and at least 25 mol %, preferably 40 mol %, of alkylenediol radicals, based on the polyester, are regarded as a particularly industrially important group of polyesters. The linear or branched alkylenediol radicals can have 2 to 12, preferably 2 to 6, C atoms and are, in particular, ethylene glycol or 1,4-butylene glycol radicals. Further monomers known for the preparation of polyesters and further polyesters are described, for example, in German Offenlegungsschrift No. 2,851,969.

Preferred polymers are the epoxide resins, thermoplastic polyesters and polyamides.

The additives can be incorporated into the polymer, for example, by a procedure in which the individual additives, together or separately, and, where relevant, further additives are mixed into the polymer by methods customary in the art, before or during shaping, or by a procedure in which the dissolved or dispersed compounds are applied to the polymer, the solvent subsequently being evaporated off is necessary. The additives can also be introduced before or during polymerisation. Relatively large amounts are advantageously incorporated by granulation in an extruder.

Examples of further additives and inert additional substances which can be used together with the flameproofing agent are antioxidants, UV stabilisers or other light stabilisers, plasticisers, lubricants, mould release assistants, nucleating agents, fluorescent brighteners, delustering agents, dyes and pigments, inert or reinforcing fillers, such as carbon black, talc, kaolin, metal powder, wollastonite, glass beads or powder, quartz powder, asbestos fibres and glass fibres, and dispersing assistants.

All types of shaped articles can be produced from the moulding compositions according to the invention. The examples which follow illustrate the invention in more detail.

(A) Preparation of the starting material

Preparation of 1,3-digylycidyl-4,5,6,7-tetrabromobenzimidazolone 44.97 g of tetrabromobenzimidazolone, 370.12 g of epichlorohydrin and 0.66 g of tetramethylammonium chloride are heated to a temperature of 140° C., with stirring, in a glass flask with a stirrer, reflux condenser and nitrogen inlet, a slight reflux being established at an internal temperature of 104° C. The water formed is separated off via a water separator. After 2½ hours, a vacuum of 55 mbars is applied and 150 ml of an azeotrope of water and epichlorohydrin are distilled off in the course of 30 minutes. This quantity is replaced again by pure epichlorohydrin. The internal temperature during this operation is 55° C.

After adding 8.8 g of NaOH in aqueous solution in the course of 2 hours, the mixture is allowed to after-react for a further 15 minutes and is then cooled to room temperature. After filtering off the precipitate with suction and further working-up carried out in the customary manner, 37 g (67.3% of theory) of 1,3-diglycidyl-4,5,6,7-tetrabromobenzimidazolone with an epoxy content of 89% and a melting point of 195°–200° C. are obtained. After two recrystallisation operations, a product with an epoxy content of 100% and a melting point of 206° C. is obtained.

(B) Preparation of the oligomeric epoxide resins

EXAMPLE 1

5.49 g of the diglycidyl compound prepared according to (A), 3.91 g of tetrabromobenzimidazolone and 25 ml of dimethylformamide as well as one drop of a 20% solution of 2-phenylimidazole in n-butanol are heated to 170° C. in a glass flask with a stirrer, nitrogen inlet and reflux condenser in the course of 2 hours. The mixture is then stirred for a further hour at 180° C. and the solvent is subsequently slowly distilled off in vacuo. Finally, the mixture is allowed to react at 200° C. for a further half an hour. The product thus formed is dried overnight at 180° C. and under 1 mbar. The resulting product has a relative viscosity of 1.04 and a decomposition point, measured thermogravimetrically, of 295° C. The maximum decomposition was at 360° C.

EXAMPLE 2

12.62 g of the diglycidyl compound prepared according to (A) and 10.92 g of tetrabromobisphenol A as well as a small drop of 20% 2-phenylimidazole solution are warmed to 230° C., with stirring, in the course of 1½ hours and the melt formed is stirred for a further 10 minutes at the above temperature in vacuo (mbar). After flushing with nitrogen, a product with a relative viscosity of 1.10 and a glass transition temperature of 166° C. is obtained. Thermogravimetric analysis gave the start of decomposition at 300° C. and a decomposition maximum at 340° C.

(C) Use Example

A molten mixture of the components below is prepared with the aid of an extruder and this mixture is then injection-moulded to form test pieces:

53% by weight of poly-1,4-butylene terephthalate with an intrinsic viscosity of 0.90 dl/g, 30% by weight of glass fibres 6 mm long, 5% by weight of antimony trioxide and 12% by weight of the product prepared according to Example 1.

The properties listed in the table which follows are measured on the test pieces (standard bars).

TABLE

| | | |
|---|---|---|
| Tensile strength DIN 53,455 | N/mm² | 115 |
| Elongation at break DIN 53,455 | % | 1.8 |
| Flexural strength DIN 53,452 | N/mm² | 180 |
| Tensile E modulus DIN 53,457 | N/mm² | 10,000 |
| Flexural E modulus ASTM D 790 | N/mm² | 8,800 |
| Impact strength DIN 53,453 | kJ/m² 23° C. | 28.5 |
| Notched impact strength DIN 53,453 | kJ/m² 23° C. | 6.8 |
| Stability to migration after 10 days at 160° C. | | no chalky appearance |
| Flammability, 0.16 cm bar UL 94 | | V-O |
| Intrinsic viscosity dl/g | | 0.79 |

The toughness properties are to be regarded as particularly good for a moulding composition provided with a flame-repellent finish.

What is claimed is:

1. A halogen-containing, essentially linear oligomeric epoxide resin of the formula I

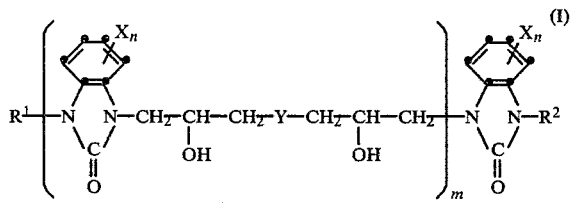

in which n is the number 2, 3 or 4, m has a numerical value from 1 to 30, X is chlorine or bromine, Y is the divalent radical of a H-acid compound from the group comprising diols, dihydric phenols, bisphenols, dicarboxylic acids and cyclic ureides and R¹ and R² are H atoms,

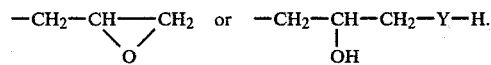

2. An epoxide resin according to claim 1, in which n is the number 3 or 4.

3. An epoxide resin according to claim 1, in which m has a numerical value from 1 to 20.

4. An epoxide resin according to claim 1, in which X is bromine.

5. An epoxide resin according to claim 1, in which Y is a divalent radical of a diol and has 2 to 12 C atoms or a divalent radical of a dicarboxylic acid and has 2 to 20 C atoms.

6. An epoxide resin according to claim 1, in which Y is a divalent radical of a bisphenol of the formula II

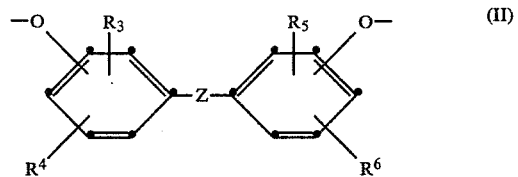

in which R³, R⁴, R⁵ and R⁶ independently of one another are a hydrogen atom, alkyl having 1–4 C atoms or a chlorine or bromine atom and Z is a direct bond, O, S, SO, SO₂, CO₂, alkylene having 1 to 8 C atoms, alkylidene having 2–8 C atoms or cycloalkylidene having 5 or 6 ring C atoms.

7. An epoxide resin according to claim 1, in which Y is a divalent radical of a cyclic ureide of one of the formulae III–VII

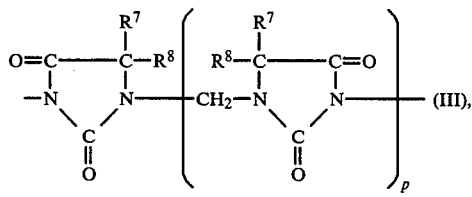

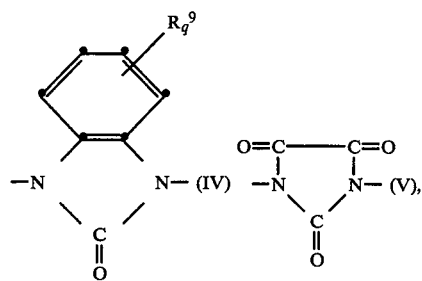

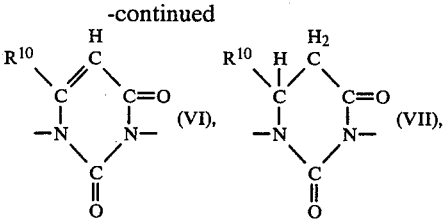

in which p is 0 or 1, q is 0 or an integer from 1 to 4, $R^7$ and $R^8$ are hydrogen atoms, phenyl or $C_1$–$C_{12}$-alkyl or $R^7$ and $R^8$ together are tetra- or penta-methylene, $R^9$ is methyl, chlorine or bromine and $R^{10}$ is a hydrogen atom or $C_1$–$C_4$-alkyl.

8. An epoxide resin according to claim 1, in which, in formula I, n is 4, m has a numerical value from 1 to 10, X is bromine and Y is a radical of the formula IV, in which $R^9$ is chlorine or bromine and q is the number 3 or 4.

9. A flame-retardant plastic composition which contains a thermosetting resin or a thermoplastic and an effective amount of an epoxide resin of the formula I according to claim 1 as a flameproofing agent.

10. A process for providing a plastic with a flame-retardant properties, which comprises incorporating an effective amount of an epoxide resin of the formula I into the plastic.

* * * * *